(12) United States Patent
Liddle

(10) Patent No.: US 7,101,179 B2
(45) Date of Patent: Sep. 5, 2006

(54) KIT AND METHOD FOR TAKING A DENTAL IMPRESSION

(75) Inventor: Katherine Liddle, Cape May Court House, NJ (US)

(73) Assignee: All Dental Prodx, LLC, Cape May Court House, NJ (US)

( * ) Notice: Subject to any disclaimer, the term of this patent is extended or adjusted under 35 U.S.C. 154(b) by 76 days.

(21) Appl. No.: 10/156,401

(22) Filed: May 28, 2002

(65) Prior Publication Data

US 2003/0224319 A1  Dec. 4, 2003

(51) Int. Cl.
*A61C 9/00* (2006.01)

(52) U.S. Cl. ........................................ 433/38

(58) Field of Classification Search ............. 433/38, 433/37, 41, 42, 34, 48
See application file for complete search history.

(56) References Cited

U.S. PATENT DOCUMENTS

| | | | | |
|---|---|---|---|---|
| 3,250,004 A | * | 5/1966 | Jones | 433/38 |
| 4,204,323 A | * | 5/1980 | Neubert et al. | 433/38 |
| 4,619,610 A | | 10/1986 | Pelerin | 433/41 |
| 4,689,010 A | | 8/1987 | Wolfe | 433/38 |
| 5,066,231 A | | 11/1991 | Oxman et al. | 433/214 |
| 5,415,544 A | * | 5/1995 | Oxman et al. | 433/48 |
| 5,513,985 A | | 5/1996 | Robertson | 433/38 |
| 5,733,118 A | * | 3/1998 | Pankuch et al. | 433/38 |
| 5,807,100 A | * | 9/1998 | Thornton | 433/48 |
| 6,749,428 B1 | * | 6/2004 | DiMarino et al. | 433/38 |

FOREIGN PATENT DOCUMENTS

| | | |
|---|---|---|
| JP | 63-270759 | 8/1988 |
| WO | 96/37162 | 11/1996 |

OTHER PUBLICATIONS

Ullmann's Encyclopedia of Industrial Chemistry, 5th Edition, vol. A8, "Dental Impression Materials", pp. 284-289, 1987.

* cited by examiner

*Primary Examiner*—Melba N. Bumgarner
(74) *Attorney, Agent, or Firm*—Kenyon & Kenyon LLP

(57) ABSTRACT

A kit for taking a dental impression comprises a thermoplastic material for bite registration on one jaw side, an impression compound for taking an impression of the opposite jaw side, and a tray for receiving the thermoplastic material on one side and the impression compound on an opposite side thereof. The tray includes a pair of opposing side walls and a flexible membrane extending therebetween, the flexible membrane defines a first receiving area and a second receiving area, the thermoplastic material is adapted to be molded to the flexible membrane and the side walls and extend past each of the side walls in order to impart sufficient rigidity to the tray.

7 Claims, 1 Drawing Sheet

KIT AND METHOD FOR TAKING A DENTAL IMPRESSION

FIELD OF THE INVENTION

The invention relates to a kit and method for taking a dental impression.

BACKGROUND OF THE INVENTION

When preparing to make a dental replacement or to carry out orthodontic measures or various restorative measures, it is necessary to take an impression of individual teeth, a number of teeth or the whole jaw. For this purpose, impression trays are used which are made of metal or a hard plastic and are filled with an elastomeric impression compound. When taking the impression, the tray encloses the tooth or teeth in an approximate U-shape and thus presses the impression compound onto the jaw area of which an impression is required.

Existing dental impression trays make it possible to take an impression of two opposite jaw sides in one operation. Examples of such existing trays are disclosed in U.S. Pat. Nos. 4,689,010 and 5,513,985. These trays have side walls which are adapted to the shape of the jaw and which are designed in such a way that, when the impression is being taken, they at least partially enclose the sides of the teeth of which an impression is required, both in the upper jaw and in the lower jaw regions. Approximately at half the height of these side walls, a flexible mesh-like layer is fixed between them. The tray is filled on both sides with an elastomeric impression compound and can thus be used for simultaneously taking an impression of the opposite jaw sides.

In principle, by allowing for the simultaneous impression taking of the upper and lower jaws, these trays permit a more accurate recording of the situation for partial or complete bite replacements. In particular, they permit registration of the counterbite, which is important for a bite replacement. In practice, however, the use of such trays is associated with problems. For reasons related to its construction (e.g., the layer that extends between the side walls comprises a non-rigid mesh-like material), existing dental impression trays are not sufficiently rigid.

When taking the impression, and in particular when removing the finished impression from the mouth, the dental impression tray can deform, so that the finished impression no longer corresponds to the conditions in the mouth. In particular, removal from the mouth can be problematic because hardened impression material often adheres to teeth with great force. Moreover, when taking the impression, there is a possibility that the bite will go as far as the flexible mesh-like layer of the tray, or may even bite completely through this, so that teeth of the upper jaw and lower jaw come into direct contact with one another and it is no longer possible to obtain an exact impression of the situation.

SUMMARY OF THE INVENTION

The object of the invention is to make available a kit and a method making it possible to take accurate and reliable dental impressions.

The kit of the present invention has three main components: a thermoplastic material for bite registration on one jaw side (opposing side); an impression compound for taking an impression of the opposite jaw side (impression side), and a tray for receiving the thermoplastic material on one side and the impression compound on an opposite side thereof. The tray preferably includes a pair of opposing side walls and a flexible membrane extending therebetween. The flexible membrane defines first and second receiving areas. The thermoplastic material is adapted to be molded to the flexible membrane and the side walls and extend past each of the side walls in order to impart sufficient rigidity to the tray.

BRIEF DESCRIPTION OF THE FIGURE

For the purpose of illustrating the invention, there is shown in the accompanying drawing a form which is presently preferred; it being understood that the invention is not intended to be limited to the precise arrangements and instrumentalities shown.

DETAILED DESCRIPTION OF THE INVENTION

Figure 1:
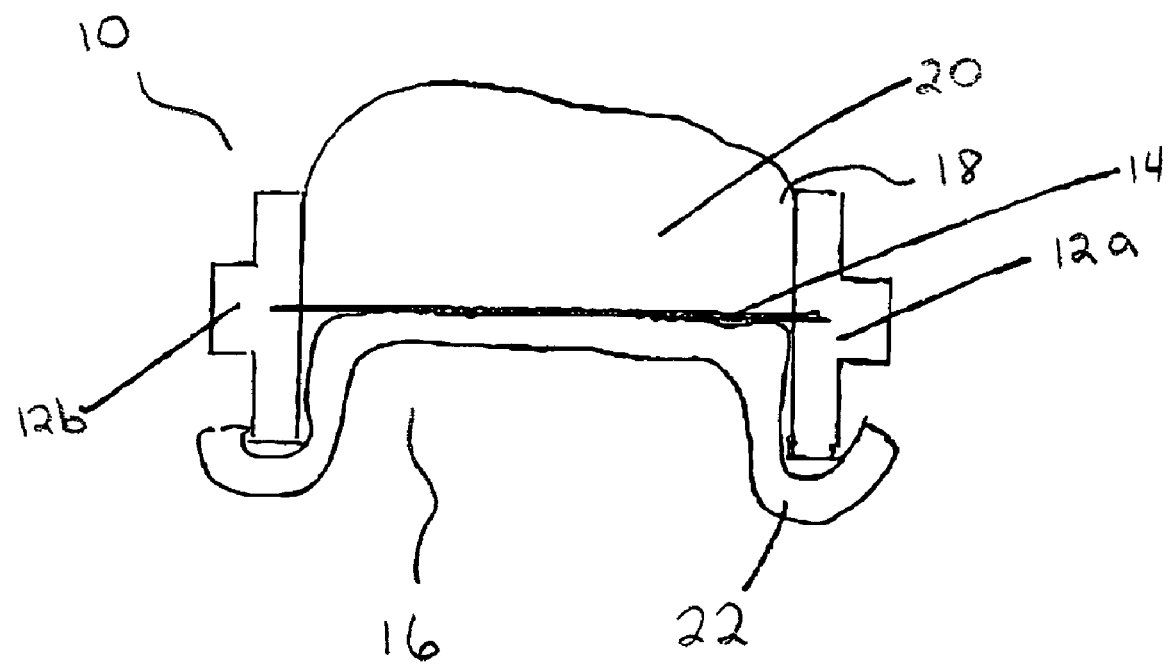
FIG. 1 is a cross-sectional view of the kit of the present invention with the thermoplastic material and impression material positioned in opposite sides of the tray.

According to the invention, a tray having a pair of spaced apart side walls is provided. The tray is divided into a first receiving area and a second receiving area by means of a flexible membrane. The tray is adapted to receive an impression compound in one of the receiving areas and a thermoplastic material in the other. The term tray denotes any arrangement which can serve as a support for receiving these two materials and can be used to introduce them into the mouth. It therefore concerns an aid making it possible and also easier to prepare for and take an impression. The tray thus has a holding function for the impression compound (particularly if the latter is free-flowing before deformation and is plastically deformable) and for the thermoplastic material (particularly in its heated softening state). The tray comprises a material or a number of materials whose properties, in particular strength, do not change, or do not change significantly, under the conditions in which the impression is taken.

The term thermoplastic material denotes. any material which, by heating to a temperature which is still tolerated by the oral tissue, is made sufficiently soft to make it possible to carry out bite registration on the thermoplastic material. Bite registration here signifies that the aim is not to obtain a complete dental impression, but only to record the position of the teeth relative to the teeth (of which a complete impression is to be taken) on the opposite jaw side. It can in particular be a thermoplastic polymer. Thermoplastic polymers comprised of polycaprolactone or polyvinyl acetate are particularly suitable. Suitable thermoplastic materials are familiar to the skilled person and are described in detail, for example, in U.S. Pat. No. 5,066,231 and Japanese Patent No. 63,270,759, the contents of which are incorporated herein by reference.

The term impression compound is to be understood as meaning any material suitable for taking a complete impression of a tooth or jaw area. Suitable free-flowing elastomers on the basis of, for example, alginates, addition-crosslinking or condensation-crosslinking silicones, polyethers or polysulfides are familiar to the skilled person and do not need to be explained further here. For example, reference is made to Ullmann's Encyclopedia of Industrial Chemistry, 5th edition, volume AB, "Dental Impression Materials" in the section "Dental Materials."

The invention permits a particularly exact recording of a bite situation. Although a complete and exact impression is taken only from one or part of one jaw side (impression side), nevertheless an exact registration of the counterbite takes place simultaneously, which is of great importance particularly for the production of a tooth replacement. The thermoplastic material hardens under the conditions in the mouth and thus stiffens the overall construction of the thermoplastic material, the tray and the impression material. If so required, the hardening can be promoted or accelerated by cooling for example with water, suitable cool packs or the like. When removing the finished impression from the mouth, the whole construction is therefore considerably more rigid than in the prior art, so that inadvertent deformation is barely possible, if at all. Moreover, when the impression is being taken, the thermoplastic material prevents complete biting-through so that the masticatory surfaces of the teeth cannot make contact with each other and distort the impression. The thermoplastic material in the softened state is also sufficiently rigid to prevent a complete biting-through.

In the context of the invention, the thermoplastic material accordingly has three simultaneous functions. First, it permits registration of the counterbite of the antagonist aspects of the teeth whose impression is to be taken. Second, it prevents biting-through, with contact between the masticatory surfaces of the opposite teeth, so that distortion of the impression is avoided. Finally, after hardening in the mouth, it stiffens the tray which is in itself somewhat unstable, and thereby prevents the impression from being distorted by deformation of the tray during or after removal from the mouth.

Before the tray is introduced into the mouth, the thermoplastic material is heated to or above its softening temperature in order to permit registration of the counterbite. Here, the tray itself then provides for sufficient strength of the component parts of the kit according to the invention, which strength is sufficient for introduction into the mouth. It is desirable for the tray to be comprised of a material that will not be softened when the heated thermoplastic material is inserted therein.

The tray includes a first receiving area for receiving the impression material. The first receiving area is defined by the opposing side walls of the tray and the flexible membrane. The side walls prevent escape of the free-flowing impression compound before and during the impression-taking. The flexible membrane may be comprised of any suitable material such as a synthetic mesh-like material, a fiber cloth, a plastic net, a knit, a gauze-like material, a plastic foil or other similar material.

Suitable trays are described in aforementioned U.S. Pat. Nos. 4,689,010 and 5,513,985, the contents of which are incorporated herein by reference.

The thermoplastic material preferably has a softening temperature which is below 80° C., more preferably 45 to 75° C., more preferably 50 to 70° C., Particularly preferably 60 to 65° C. In the context of the invention, softening temperature signifies that the material is sufficiently soft at this temperature to permit bite registration.

The thermoplastic material is preferably sufficiently shape-stable at 37° C. (body temperature) to retain the bite registration. Sufficient shape stability signifies that the thermoplastic material, upon removal of the impression from the mouth, does not deform or does so only to an extent that still ensures sufficiently accurate counterbite registration. Preferably, the thermoplastic material is of a sufficient size so that, when in the softened state, it may encompass one side of the tray and extend over the side walls of the same. This ensure that the tray will be sufficiently rigid once the thermoplastic material cools and hardens.

The method according to the invention for taking a dental impression and simultaneously registering the counterbite comprises the following steps:

a) providing a thermoplastic material, an impression compound and a tray, the tray having a pair of opposing side walls and a flexible membrane extending between the side walls, the flexible membrane forming a first receiving area and a second receiving area, b) heating the thermoplastic material to at least the softening temperature, c) introducing the thermoplastic material into one side of the tray so that it encompasses the same and extends over the side walls of the tray, d) introducing the impression material into the opposite side of the tray, and e) taking the impression and registering the counterbite.

The sequence of method steps is not critical here.

It is important that before the tray is placed in the mouth, the impression compound is arranged in one of the receiving areas of the tray and the thermoplastic material, which is heated to a softened state, is arranged in the other. Thus, it is readily possible to introduce the impression compound into the tray before the thermoplastic material, or to heat the thermoplastic material only after introduction into the tray.

Finally, the invention also relates to a method for preparing a tray for taking a dental impression and simultaneously registering the counterbite, which method comprises the following steps:

a) providing a thermoplastic material, an impression compound and a tray, the tray having a pair of opposing side walls and a flexible membrane extending between the side walls, the flexible membrane forming a first receiving area and a second receiving area, b) heating the thermoplastic material to at least the softening temperature, c) introducing the thermoplastic material into one side of the tray so that it encompasses the same and extends over the side walls thereof, d) introducing the impression material into the opposite side of the tray.

Here too, the sequence of steps is not critical.

The methods according to the invention do not necessarily have to be carried out with a kit according to the invention. It is equally possible to obtain commercially available impression compounds, trays and thermoplastic materials separately and to combine them in order to carry out the methods according to the invention.

The thermoplastic material utilized in the present invention is preferably in the form of a plate whose dimensions are especially suitable for insertion into a tray. As set forth above, it is preferred that the thermoplastic material be sized and shaped so that, when heated, it can be positioned in one side of the tray and extend over the edge of the side walls thereof. The thermoplastic material must be of sufficient dimension to record a detailed impression of the opposing teeth and muscle structure of a patient's mouth. It is preferable for the thermoplastic material be at least approximately 0.35 cm thick. In one preferred embodiment the thermoplastic material, prior to being heated and softened, is oblong shaped and has a thickness of approximately 0.4 cm, a width of approximately 4 cm and a length of approximately 7.25 cm. In another preferred embodiment the thermoplastic material, prior to heating and softening, is arcuately shaped so as to approximate the shape of the quadrant of the arch of the patient's mouth.

An illustrative embodiment of the invention is explained in more detail below with reference to the drawing which shows a cross section through a tray according to the invention provided with impression compound and thermoplastic material.

Referring to FIG. 1, a dental impression tray 10 having a pair of opposing side walls 12a and 12b, respectively, is shown. A flexible membrane 14 extends between the opposing side walls 12a and 12b. Such trays are, in general, commercially available. The flexible membrane forms a pair of opposing receiving areas 16 and 18. One receiving area is filled with a conventional impression material 20. A thermoplastic material 22 is heated to above the softening temperature and introduced into the opposing receiving area of the tray. As can be seen from the drawing, the thermoplastic material is molded to the flexible membrane 14 and the side walls 12a and 12b and protrudes past an edge of each of the side walls.

With the tray prepared in this way, an impression is taken in the mouth of a patient. The thermoplastic material accurately records the deformation and holds that shape so that the finished impression accurately corresponds to the condition of the mouth. The tray remains in the mouth until the impression compound 20 is sufficiently hardened and the thermoplastic material 22 is cooled approximately to body temperature and is thereby likewise hardened again. In this hardened state, the thermoplastic material 22 following the course of flexible membrane 14 and side walls 12a and 12b of the tray forms a strengthening layer which increases the rigidity of the whole tray (in particular also the side walls).

The tray is then removed. An impression of a jaw side (impression side) has formed in the impression compound 20, and the thermoplastic material has registered the counterbite in the opposing side of the tray.

The present invention may be embodied in other forms without departing from the spirit or essential attributes thereof and accordingly reference should be made to the claims rather than the foregoing specification as indicating the scope thereof.

What is claimed is:

1. A kit for taking a dental impression, comprising a thermoplastic material for bite registration on one jaw side, an impression compound for taking an impression of the opposite jaw side, and a tray for receiving the thermoplastic material on one side and the impression compound on an opposite side thereof, the tray includes a pair of opposing side walls and a flexible membrane extending therebetween, the flexible membrane defines a first receiving area and a second receiving area, wherein the thermoplastic material is molded to one side of the flexible membrane and the side walls, and completely extends over an outermost surface of each of the side walls in order to impart sufficient rigidity to the tray, wherein the outermost surface of each of the side walls is determined in a direction perpendicular to the flexible membrane.

2. The kit of claim 1, wherein the flexible membrane is comprised of a synthetic mesh-like material.

3. The kit of claim 1, wherein the thermoplastic material has a softening temperature of 45–75° C., and is sufficiently shape-stable at approximately 37° C. to retain the bite registration.

4. The kit of claim 1, wherein the thermoplastic material comprises polycaprolactone or polyvinyl acetate.

5. The kit of claim 1, wherein the thermoplastic material is at least approximately 0.35 cm thick.

6. A method for taking a dental impression and at the same time registering the counterbite, comprising the steps of:
   a) providing a thermoplastic material, an impression compound and a tray, the tray having a pair of opposing side walls and a flexible membrane extending between the side walls, the flexible membrane forming a first receiving area and a second receiving area,
   b) heating the thermoplastic material to at least the softening temperature thereof,
   c) introducing the heated thermoplastic material into one of the receiving areas so that the heated thermoplastic material covers one side of the flexible membrane and completely extends over an outermost surface of each of the side walls of the tray, wherein the outermost surface of each of the side walls is determined in a direction perpendicular to the flexible membrane,
   d) introducing the impression compound on the opposite side of the flexible membrane into the other one of the receiving areas,
   e) taking the impression and registering the counterbite.

7. A method for preparing a tray for taking a dental impression and at the same time registering the counterbite, comprising the steps of:
   a) providing a thermoplastic material, an impression compound and a tray, the tray having a pair of opposing side walls and a flexible membrane extending between the side walls, the flexible membrane forming a first receiving area and a second receiving area,
   b) heating the thermoplastic material to at least the softening temperature thereof,
   c) introducing the heated thermoplastic material into one of the receiving areas so that the heated thermoplastic material covers one side of the flexible membrane and completely extends over an outermost surface of each of the side walls of the tray, wherein the outermost surface of each of the side walls is determined in a direction perpendicular to the flexible membrane,
   d) introducing the impression compound on the opposite side of the flexible membrane into the other one of the receiving areas.

* * * * *